United States Patent
Strait et al.

(10) Patent No.: US 8,490,471 B1
(45) Date of Patent: Jul. 23, 2013

(54) BENCH TEST SCREENING METHOD FOR FLUID ANTIFOAM ADDITIVES

(75) Inventors: Kevin M. Strait, Richmond, VA (US); Chintan N Ved, Canton, MI (US)

(73) Assignees: Afton Chemical Corporation, Richmond, VA (US); Ford Global Technologies, LLC, Dearborn, MI (US)

( * ) Notice: Subject to any disclaimer, the term of this patent is extended or adjusted under 35 U.S.C. 154(b) by 36 days.

(21) Appl. No.: 13/427,965

(22) Filed: Mar. 23, 2012

(51) Int. Cl.
*G01N 37/00* (2006.01)
*G01N 33/62* (2006.01)

(52) U.S. Cl.
USPC ........................................ 73/60.11; 73/53.05

(58) Field of Classification Search
USPC .................. 73/53.05, 10, 19.1, 19.11, 53.01, 73/54.03, 60.11
See application file for complete search history.

(56) References Cited

U.S. PATENT DOCUMENTS

| | | | | |
|---|---|---|---|---|
| 2,315,983 A * | 4/1943 | Ross et al. | ................... | 73/60.11 |
| 2,380,679 A * | 7/1945 | Smith | .......................... | 73/60.11 |
| 2,435,205 A * | 2/1948 | Davis et al. | ................... | 516/115 |
| 5,375,459 A * | 12/1994 | Gerke et al. | ................. | 73/60.11 |
| 7,926,327 B2 * | 4/2011 | Schmidt | ...................... | 73/60.11 |
| 2011/0111996 A1* | 5/2011 | Lakes et al. | .................. | 508/496 |
| 2012/0096930 A1* | 4/2012 | Ortiz et al. | .................. | 73/60.11 |

\* cited by examiner

*Primary Examiner* — Daniel Larkin
*Assistant Examiner* — Jamar Ray
(74) *Attorney, Agent, or Firm* — Luedeka Neely Group, P.C.

(57) ABSTRACT

A method for evaluating antifoam additives for lubricants. The method includes a step of aging a quantity of fluid containing an antifoam additive in one or more high shear simulator(s) for a period of time to provide an aged fluid. After the aging step, the fluid is evaluated in a foam tendency evaluation test to provide the foaming tendency for the fluid.

13 Claims, No Drawings

BENCH TEST SCREENING METHOD FOR FLUID ANTIFOAM ADDITIVES

TECHNICAL FIELD

The disclosure relates to the field of evaluating additives for power drive fluids and in particular to a bench test method for evaluating service life for anti-foam additives for transmission fluids.

BACKGROUND AND SUMMARY

Automotive driveline systems include complex gear trains and turbomachinery that rely on petroleum products to provide a hydraulic working fluid and lubricant. Specifically, passenger car automatic transmissions and transaxles use turbines, pumps, gears and clutches operating at high speed and high temperature in a lubricant. The high speed rotation and high power densities of these systems, combined with the air space in the system and air entrained in the lubricant, may result in the formation of foam. Foam, consisting of a small quantity of lubricant and a large quantity of air, compromises pump efficiencies by changing the compressibility of the lubricant. As a result, pistons and valves actuated by the lubricant may not function correctly if the air content of the working fluid is large. Furthermore, the gear trains may receive inadequate lubrication, due to low pump efficiencies and a reduced capacity for the lubricant to provide a cooling effect, if a foam condition exists. Modern designs of drivetrain hardware are trending towards small sumps and higher power throughput densities, and relying upon less lubricant in general than prior designs. A lower lubricant volume may compound the challenge of dispelling foam from drivetrain system under operating conditions over a period of time.

Most industries find it necessary to modify the lubricant with chemical additives to dispel foam, prevent air entrainment, or both. Such additives usually function by modifying the surface tension of the lubricant relative to air, and/or by introducing insoluble film-tension modifiers that promote the collapse of air bubbles in standing foam. The additives dispel air from the lubricant in a sump or similar location where air and lubricant interface by reducing the stability of the thin film of lubricant forming the walls of each bubble in standing foam.

A conventional method for evaluating transmission fluid additives includes the use of production vehicles, and a dynamometer and operation of the vehicles on the fluid containing the additives for many thousands of miles. The dynamometer test and vehicles may be used simulate extended and/or intense real-world service for the fluid and therefore may be used to evaluate additives for transmission fluids. However, in the case of antifoam additives, such conventional evaluation methods are extremely expensive and time consuming, particularly when evaluating a large number of different antifoam additives. Accordingly, there exists a need for a bench scale antifoam additive evaluation test providing results that correlate well with the expensive and time consuming vehicle tests.

According to embodiments of the disclosure, there is provided a method for evaluating antifoam additives for lubricants. The method includes a step of aging a quantity of fluid containing an antifoam additive in one or more high shear simulator(s) for a period of time to provide an aged fluid. After the aging step, the fluid is evaluated in a foam tendency evaluation test to provide the foaming tendency for the fluid.

In another embodiment, the disclosure provides a bench scale method for screening antifoam additives for lubricant compositions. The method includes aging a fluid containing an antifoam additive for at least about 5 hours in one or more high shear simulator(s), collecting fluid from the simulator(s) after aging foam testing the fluid, and determining a foaming tendency in the fluid.

In one embodiment, the high shear simulator(s) are selected from the group consisting of a tapered roller bearing simulator, a sonic irradiation tool, a fuel injector shear apparatus, and the like.

An advantage of the screening test according to the disclosure is that the test may provide a quicker and less expensive method for evaluating the ability of antifoam additives to dispel foam in a lubricant over the life of the lubricant. Another advantage of the screening test is that fluids containing antifoam additives may be evaluated under more closely controlled conditions than are possible with conventional vehicle tests thereby providing more accurate evaluation of the antifoam additives.

DETAILED DESCRIPTION

According to embodiments of the disclosure, lubricant fluids for use in drivetrains may be evaluated before and after service, through laboratory techniques, in order to determine the fluids' ability to dispel foam over the intended service life of the fluid. Such evaluations are typically conducted on fresh fluids that have not been used in vehicles or on fluids that have been used under non-severe conditions. However, it has been observed that severe service in a common automatic transmission may affect a drivetrain fluid making the fluid incapable of meeting pre-established "passing" criteria under the foam tendency tests, even if the same lubricant product passed these tests easily when new.

The foregoing methods may also be conducted using a modified technique where a high-speed mechanical dispersion device is applied to the fluid sample to re-distribute the anti-foam additives prior to conducting the foam test. Historically, pre-treating the lubricant sample with a high-speed blender commonly lead to "passing" or acceptable anti-foam performance in lubricants that have been used under extended or harsh service. Modern transmission designs may produce sufficient forces on the drivetrain fluid to degrade the anti-foam performance of the fluid to a point where the optional dispersion treatment no longer improves the antifoam performance as measured in the laboratory. Modern transmissions may degrade the antifoam performance of a particular lubricant such that no laboratory technique is capable of producing a "passing" result on that fluid. In other words, the anti-foam efficacy of the fluid may be destroyed through severe service.

In order to provide additives that maintain the antifoam performance of a fluid over the service life of the fluid, it is desirable to evaluate and compare a large number of different antifoam additives to provide a selection of antifoam additives that resist or avoid degradation under severe service conditions. It is also desirable to be able to evaluate the additives under laboratory conditions without the need for using production vehicles and dynamometers to provide aged fluids for antifoam evaluation.

Accordingly, a laboratory technique, as described herein, may be used to apply mechanical forces, such as high shear forces, to a fluid to simulate aging of the fluid provided by a vehicle test. One technique for applying high shear forces uses a tapered roller-bearing simulator, the use of which is described in DIN 51350-6/CEC L-45-T-93 method C, to provide an aged fluid. The tapered bearing simulator is used conventionally to determine the ability of viscosity index improvers to maintain the viscometric properties of the fluids under high load conditions found in roller bearings. The foregoing techniques used to evaluate durable viscosity modifiers are typically conducted by processing a small (~30 mL) sample of fluid for relatively short period of time (a few tens of hours).

The process of applying the tapered bearing simulator to reproduce anti-foam degradation has been found to require treatment on a similar time scale to that used for evaluating the viscometric properties of the fluid. However, the quantity of fluid for foam testing requires that numerous small samples of fluid ranging from about 15 to about 30 mL be discretely processed in the tapered bearing simulator and combined to allow comparison of pre and post treatment performance of antifoam additives. It is anticipated that a researcher skilled in the relevant arts may develop a suitable method of aging or processing a large quantity at one session, either by the extension of treatment time or by another suitable means. The tapered roller bearing simulator is operated according to DIN 51350-6 or CEC L-45-T-93(C) for at least about 15 continuous hours, suitably from about 15 to about 25 hours under of a load of from about 30 to about 50 kilograms to provide an aged fluid. A circulating chiller with a suitable cooling fluid held at a temperature ranging from about 30 to about 50° C. may be pumped through coolant pathways in a bulkhead for the bearing at a rate ranging from about 1.8 to about 8 liters per minute. At the conclusion of the operating time for the tapered roller bearing simulator, the aged fluid is collected in a container until a sufficient total is processed through the tapered bearing simulator. Some light mixing of the collected sample may be used to ensure homogeneity of the final sample.

Alternatively, substitute aging techniques commonly understood to affect a lubricant sample in a way similar to that of a tapered roller bearing simulator may also be used. For example, a sonic shear tool of the general type described by ASTM method D2603 may be used instead of the tapered roller bearing simulator. Additional examples of high shear simulators may include, but are not limited to, a high-pressure injector shear test according to ASTM method D5275, or certain kinds of extended pump tests. Those skilled in the art may substitute other shear-based aging mechanisms or service life simulators for the foregoing in order to achieve an outcome commensurate with this disclosure.

Next, the foaming tendency of the collected fluid is measured with and without the pre-treatment in a high-speed blender, described above. The foaming tendency of the fluid may also be conducted on fresh (un-aged) fluid to determine any differences in antifoam performance between a fresh fluid sample and the aged fluid sample.

The foaming tendency procedure includes charging the fluid to a suitable graduated clear glass or plastic vessel that is taller than it is wide. The liquid should be at least 5 cm in total depth in the vessel, or at least a depth sufficient to cover a small gas-inlet diffuser made of porous material such that the pores are generally less than 80 microns in diameter. The diffuser should be capable of passing 3 or more liters per minute of dry air under less than 1 psi pressure differential when connected to a compressed air supply and vented to the atmosphere. Dry air is metered through the diffuser at a rate previously established to reveal an equilibrium foaming characteristics of the liquid sample, while the temperature of the sample is controlled to reveal the foaming characteristics as they relate to the lubricant's intended use.

In general, low foam volumes are desired, with application-specific limits on the equilibrium volume of foam that is measured in the vessel. Large increases in the equilibrium foam volume of a given lubricant as a result of the tapered roller bearing simulator, for a given combination of lubricant quantity, air flow and inspection temperature indicate the service life simulation has degraded the foam prevention capabilities of the lubricant.

The following non-limiting examples and comparative data may demonstrate the ability of the disclosed techniques to evaluate the antifoam performance of a fluid containing an antifoam additive.

In the following tables, the foaming tendency of a non-antifoam durable fluid formulation and of an antifoam durable fluid formulation are compared before and after aging according to the aging technique described above.

TABLE 1

|  | Non-Antifoam Durable Formulation | | Antifoam Durable Formulation | |
| --- | --- | --- | --- | --- |
|  | Fluid A | Fluid A After aging | Fluid B | Fluid B After aging |
| Low air flow through diffuser Ambient temperature (equilibrium foam in mL) | 5 | 440 | 10 | 25 |
| Low air flow through diffuser Elevated temperature (equilibrium foam in mL) | 30 | 65 | 5 | 35 |
| Low air flow through diffuser Ambient temperature after elevated temperature (equilibrium foam in mL) | 5 | 460 | 5 | 15 |
| High air flow through diffuser Maximum service temperature (equilibrium foam in mL) | 60 | 95 | 50 | 80 |

The table above (Table 1) demonstrates the typical performance of un-aged and aged fluids in the foam tests. The table below (Table 2) provides a similar comparison of un-aged and aged fluids wherein a laboratory blender was used to pre-treat the samples before foam testing. Fluid A was a fluid containing mechanically-vulnerable antifoam additive and Fluid B was a fluid containing a mechanically-durable antifoam additive. The methods allow for a generous margin of repeatability and reproducibility. Therefore only gross changes in antifoam performance are the most meaningful.

TABLE 2

|  | Non-Antifoam Durable Formulation | | Antifoam Durable Formulation | |
| --- | --- | --- | --- | --- |
|  | Fluid A | Fluid A After aging | Fluid B | Fluid B After aging |
| Low air flow through diffuser Ambient temperature (equilibrium foam in mL) | 0 | 460 | 0 | 0 |
| Low air flow through diffuser Elevated temperature (equilibrium foam in mL) | 40 | 60 | 5 | 20 |
| Low air flow through diffuser Ambient temperature after elevated temperature (equilibrium foam in mL) | 0 | 460 | 0 | 5 |
| High air flow through diffuser Maximum service temperature (equilibrium foam in mL) | 60 | 110 | 30 | 55 |

In both tables, Fluid A showed suitable antifoam performance before aging but failed the foam tests after aging. Fluid B showed suitable antifoam performance before and after aging. Accordingly, the foregoing aging technique may be used to evaluate additives in a rapid, less expensive way in order to determine additives that can provide suitable antifoam performance over the service life of the fluid.

Other embodiments of the present invention will be apparent to those skilled in the art from consideration of the specification and practice of the invention disclosed herein. As used throughout the specification and claims, "a" and/or "an" may refer to one or more than one. Unless otherwise indicated, all numbers expressing quantities of ingredients, properties such as molecular weight, percent, ratio, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. It is intended that the specification and examples be considered as exemplary only, with a true scope and spirit of the invention being indicated by the following claims.

What is claimed is:

1. A method for evaluating antifoam additives for lubricants comprising:
   aging a quantity of fluid containing an antifoam additive in one or more shear simulator(s) selected from the group consisting of a tapered roller bearing simulator, a sonic irradiation tool, and a fuel injector shear apparatus for a period of time to provide an aged fluid; and
   evaluating the fluid in a foam tendency evaluation test to provide the foaming tendency for the fluid.

2. The method of claim 1, wherein the period of time for aging the quantity of fluid is at least about 5 hours.

3. The method of claim 1, wherein the shear simulator(s) comprises tapered roller bearing simulator(s), wherein the bearing load ranges from about 30 to about 50 kilograms.

4. The method of claim 3, wherein the quantity of fluid ranges from about 15 to about 50 mL per tapered roller bearing simulator.

5. The method of claim 1, wherein the foam tendency evaluation test is conducted by metering air or nitrogen through a diffuser into the fluid to foam the fluid.

6. The method of claim 1, wherein the foam tendency evaluation test is conducted using a blender to pre-treat the fluid before the foam tendency evaluation test.

7. A bench scale method for screening antifoam additives for lubricant compositions comprising:
   aging a fluid containing an antifoam additive for at least about 5 hours in one or more shear simulator(s) selected from the group consisting of a tapered roller bearing simulator, a sonic irradiation tool, and a fuel injector shear apparatus,
   collecting fluid from the simulator(s) after aging,
   causing and monitoring foam in the fluid, and
   determining a quantity of foam generated in the fluid.

8. The method of claim 7, wherein the shear simulator(s) comprises a tapered bearing simulator wherein a housing of the tapered bearing simulator is cooled with a cooling fluid during the aging step.

9. The method of claim 8, wherein the cooling fluid for the housing is maintained at a temperature ranging from about 30 to about 70° C.

10. The method of claim 8, wherein the load ranges from about 30 to about 50 kilograms.

11. The method of claim 7, wherein multiple quantities of fluid are aged in the one or more shear simulator(s) and the quantities are combined to provide larger total quantities for subsequent evaluation.

12. The method of claim 7, wherein air is introduced into the fluid below a liquid level of fluid in a graduated cylinder to foam the fluid.

13. The method of claim 7, wherein a blender is used to pre-treat the fluid.

* * * * *